US006729205B2

(12) United States Patent
Phillips (10) Patent No.: US 6,729,205 B2
(45) Date of Patent: May 4, 2004

(54) MULTI-POSITION RATCHET MECHANISM

(76) Inventor: Burns P. Phillips, 1838 Elm Hill Pike, Nashville, TN (US) 37210

(*) Notice: Subject to any disclaimer, the term of this patent is extended or adjusted under 35 U.S.C. 154(b) by 5 days.

(21) Appl. No.: 10/113,663

(22) Filed: Mar. 28, 2002

(65) Prior Publication Data

US 2002/0152833 A1 Oct. 24, 2002

Related U.S. Application Data

(60) Provisional application No. 60/279,395, filed on Mar. 28, 2001.

(51) Int. Cl.[7] .................................................. G05G 1/04
(52) U.S. Cl. ....................... 74/577 M; 74/575; 600/227
(58) Field of Search ............................... 74/575, 577 R, 74/577 S, 577 M; 600/215, 227, 228, 229, 230

(56) References Cited

U.S. PATENT DOCUMENTS

| | | | | |
|---|---|---|---|---|
| 2,670,732 A | * | 3/1954 | Nelson ........................ 600/234 |
| 3,965,890 A | * | 6/1976 | Gauthier ...................... 600/215 |
| 4,254,763 A | * | 3/1981 | McCready et al. ............ 128/20 |
| 4,421,108 A | * | 12/1983 | Cabrera et al. .............. 600/234 |
| 4,424,724 A | * | 1/1984 | Bookwalter et al. ........... 74/540 |
| 5,375,481 A | * | 12/1994 | Cabrera et al. ........... 74/577 M |
| 5,755,660 A | * | 5/1998 | Tyagi .......................... 600/205 |
| 5,893,831 A | * | 4/1999 | Koros et al. ................. 600/232 |
| 6,042,542 A | * | 3/2000 | Koros et al. ................. 600/231 |
| 6,241,659 B1 | * | 6/2001 | Bookwalter et al. ......... 600/231 |
| 6,431,025 B1 | * | 8/2002 | Koros et al. ............. 74/577 M |
| 6,537,212 B2 | * | 3/2003 | Sherts et al. ................. 600/205 |

* cited by examiner

*Primary Examiner*—David A. Bucci
*Assistant Examiner*—Vicky A. Johnson
(74) *Attorney, Agent, or Firm*—Stephen J. Stark; Miller & Martin LLP (57) ABSTRACT

A multi-position ratchet mechanism has a retractor holder which receives a retractor stem connected to a retractor. A pawl selectively engages the retractor stem to allow for the retractor stem to be positioned relative to the retractor holder. The retractor holder has a passage and is connected at a base pivot to a base having a toothed hub. The toothed hub extends into the passage and a locking mechanism connected to the retractor holder allows for the selection of a pivot angle of the retractor holder relative to the base. The base rotates relative to a ring holder in a first configuration. In a second configuration a rotation angle between the base and the ring holder is set and locked with a locking actuator. The locking actuator is a cam actuator with drives a cam surface about a locking pivot to allow contact surface between the base and the ring holder to contact one another. A retaining mechanism selectively maintains a ring in a slot in the ring holder.

23 Claims, 6 Drawing Sheets

MULTI-POSITION RATCHET MECHANISM

CLAIM OF PRIORITY

This application claims the benefit of U.S. Provisional Patent Application No. 60/279,395 filed Mar. 28, 2001.

FIELD OF THE INVENTION

The present invention relates to a multi-position ratchet mechanism for holding a surgical retractor blade and, more particularly to a quick-release ratchet mechanism which permits the retractor blade to be tilted and rotated into the wound so that the organ may be retracted and lifted at the same time.

BACKGROUND OF THE INVENTION

A surgical retraction systems is described in U.S. Pat. No. 4,254,763. This patent, incorporated by reference, describes the ability to utilize a retractor ring to retract organs in the plane of the ring.

An improvement for use with the ring of U.S. Pat. No. 4,354,763 was disclosed in U.S. Pat. No. 4,424,724. The '724 Patent, also incorporated by reference, discloses a multi-position ratchet mechanism for holding a surgical retractor blade allowing the blade to be pivoted into the wound from a ring and retracted at the same time. This device allowed the retractor to be tilted, or pivoted, into the wound and retracted with one motion.

The ratchet mechanism of the '724 patent only allows for pivoting in a single plane about the ratcheting mechanism perpendicularly to the ring to which the mechanism is secured. A need exists for rotation in other planes as well, preferably in a plane substantially perpendicular to the plane of the operation of the ratcheting mechanism, i.e., the plane of pivoting, or the plane of the ring.

Furthermore, the ratchet mechanism of the '724 patent is not believed to adequately secure the retractor to the ring. Specifically, the ratchet holder relies on tension of the retractor blade to pull the holder forward so that the edge of a dowel pin engages indentations of the ring to prevent the circumferential sliding of the ratchet holder and to prevent the ratchet holder from falling off the ring. However, there are instances when this necessary tension may not be present or adequate and the ratchet holder would have little, if any, resistance to prevent coming off the ring. Furthermore, torque applied to the ratchet holder may also cause problems. Accordingly, a need exists to restrain the ratchet holder from moving away off of the ring.

SUMMARY OF THE INVENTION

The multi-position ratchet mechanism of the preferred embodiment provides a multi-position ratchet mechanism for holding the retractor blade for permitting it to be pivoted into a wound and retracted at the same time which may be thought to simulate the natural "toe-in" method of retraction one could achieve with the hand. The mechanism of the present invention also permits the position of the ratchet mechanism to be moved circumferentially about the support ring and allow for rotation about the selected position relative to the support ring. Furthermore the ratchet mechanism is preferably configured to securely connect with the support ring.

The multi-position ratchet mechanism includes a ring holder, which is mounted onto the support ring, such as an oval support ring. Selective positioning of the ratchet holder relative to the ring may be achieved through the use of a transverse slot in the ratchet holder which receives a thickness of the ring therein. A retention mechanism is utilized to prevent the ring from inadvertently coming out of the transverse slot.

The retention mechanism restrains the ring in the transverse slot of the ring holder. Specifically, the ring typically has a width which terminates proximate to the end transverse slot when the ring is installed in the transverse slot. The retention mechanism is moved into position to prevent movement of the ring out of the transverse slot. In the preferred embodiment, the retention mechanism is pivoted in and out of position with a lever.

The multi-position ratchet also preferably includes the ability to rotate relative to the ring as well as the ability to be secured in a fixed radial orientation relative to the ring upon rotation to a desired angle. Opposing serrated washers which cooperate to resist rotation when engaged maybe utilized. The serrated washers maybe engaged or disengaged utilizing a cam, or otherwise.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
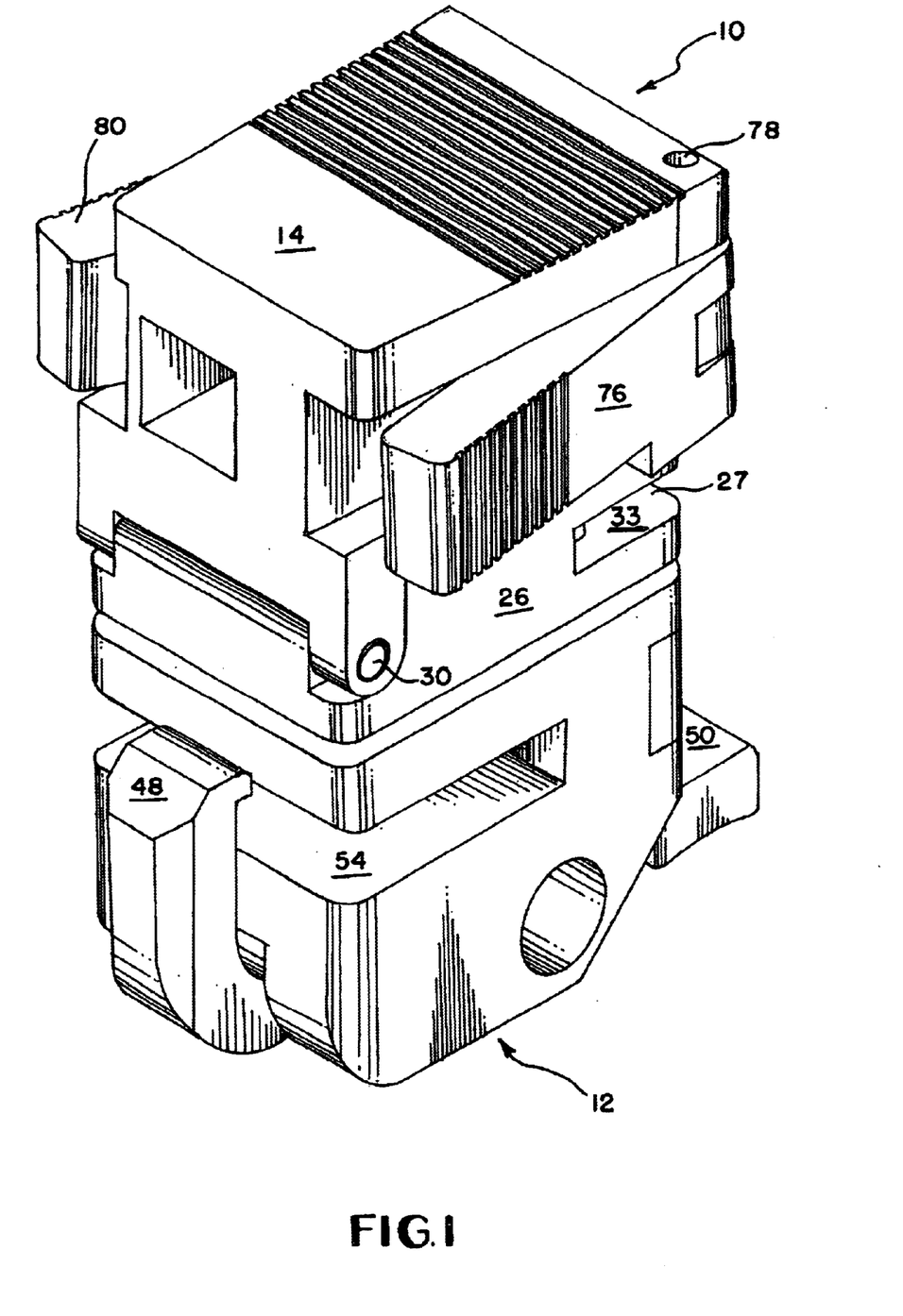
FIG. 1 shows a top elevational view of the multi-position ratchet mechanism of the present invention.

The multi-position ratchet mechanism 10 of FIGS. 1–4 maybe utilized in place of the mechanisms illustrated in FIG. 1 of U.S. Pat. No. 4,424,724. However, the multi-position ratchet mechanism 10 of the presently preferred embodiment is believed to improve on the basic design of the prior art ratchet mechanism.

Figure 3:
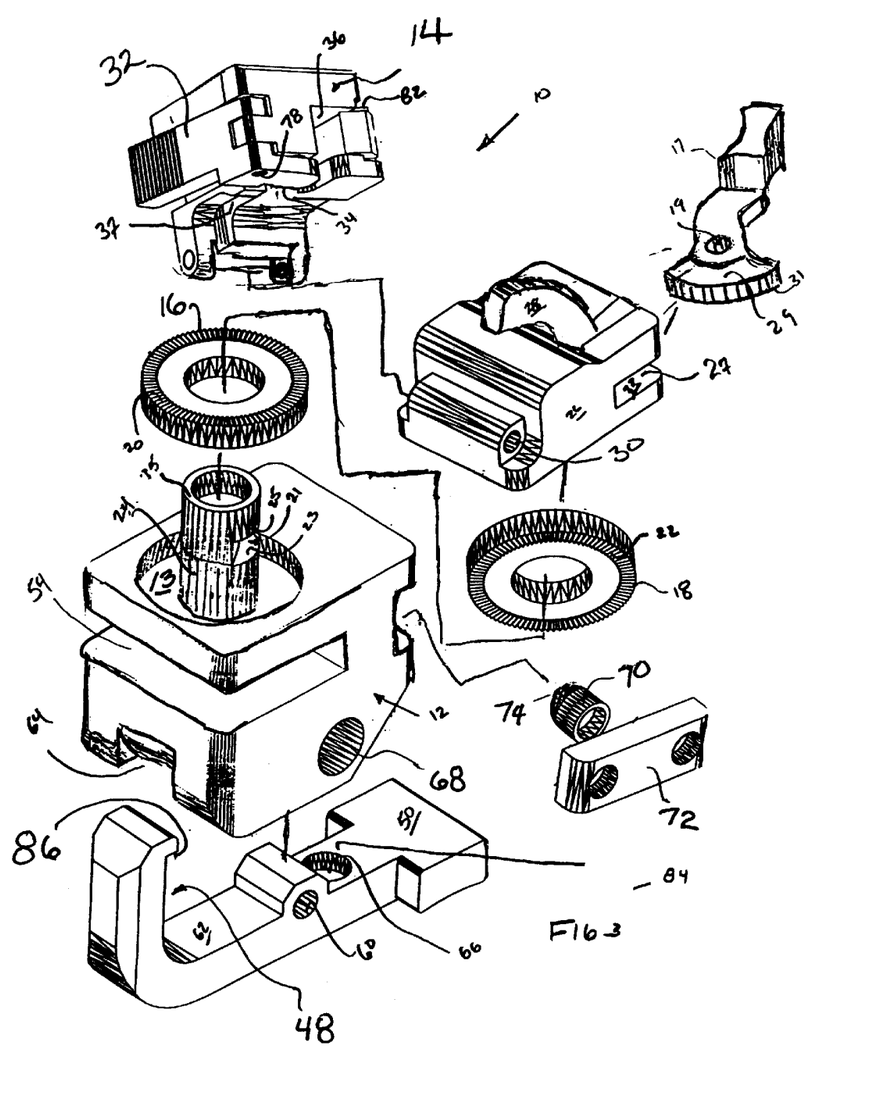
FIG. 3 shows a partially exploded perspective view of the mechanism of FIG. 1.

The ratchet mechanism 10 has a ring holder 12 connected to a retractor holder 14. The retractor holder 14 may be pivoted up and down to place a retractor blade (not shown) at a desired depth. Furthermore, the ring holder 12 may be rotated relative to the ratchet holder 14. Specifically, the illustrated ring holder 12 rotates about axle 15 shown in FIG. 3. A pair of opposing washers 16, 18 oppose one another, and in a first configuration are spaced from one another, and in a second configuration contact one another as described in more detail below. The washer 16 may be press fit into well 13 as illustrated in FIG. 3. Washer 18 may similarly be connected to base 26.

Figure 2:
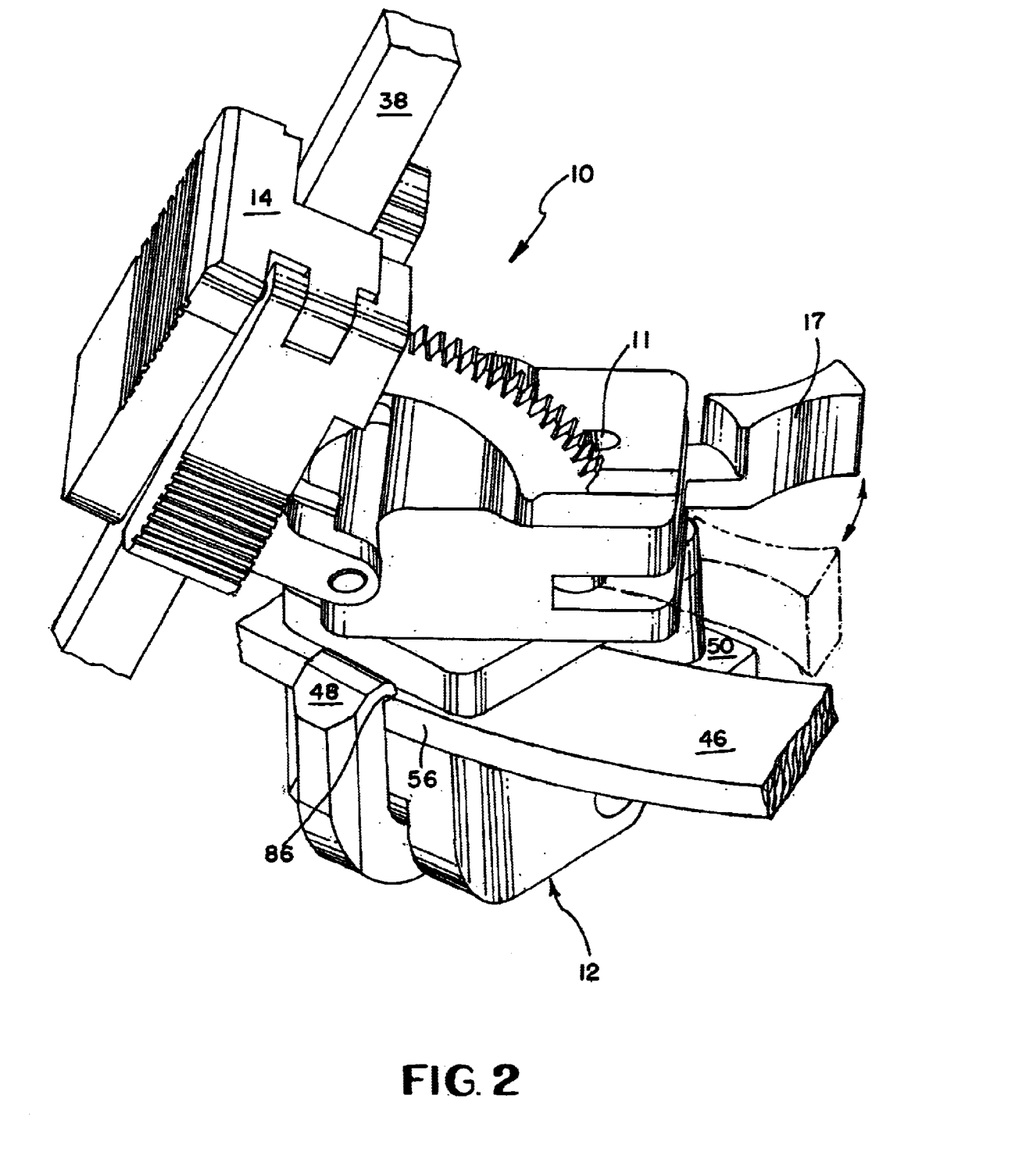
FIG. 2 shows a top elevational view of the multi-position ratchet mechanism of FIG. 1 connected to a retractor stem and a ring, and showing both horizontal and vertical plane rotation; operation of the cam actuator is shown in phantom.
Figure 4:
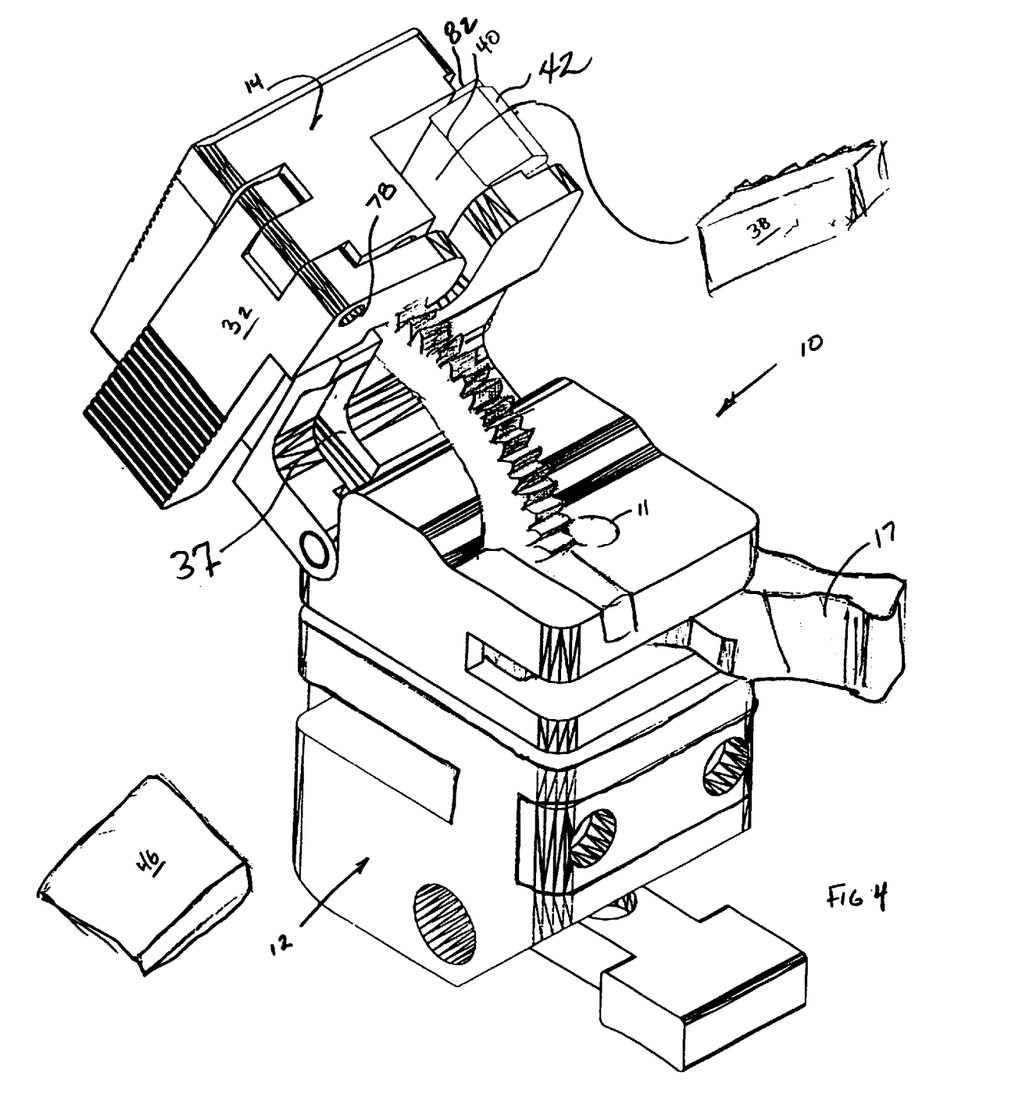
FIG. 4 shows a top elevational view of the mechanism of FIG. 1 showing vertical plane rotation.

In FIGS. 1, 2 and 4 the rotational element is located in the first configuration. The washers 16,18 have serrations 20,22 on opposing faces (as illustrated in FIG. 3) which cooperate to prevent the ring holder 12 from rotating relative to the retractor holder 14 when in the second configuration shown in phantom in FIG. 2. In FIGS. 1,2, and 4 the washers 16,18 are spaced apart from one another a sufficient distance to allow the retractor holder 14 to rotate about the axle 15 relative to the ring holder 12. A spring 24 may be utilized to preferentially maintain the washers 16,18 in either the first or the second position. In the preferred embodiment, the washers 16, 18 are biased in the first configuration. When the radial alignment of the retractor holder 14 relative to the ring holder 12 is to be changed, the operator moves the washers 16,18 apart to the first configuration such as by locating the cam actuator 17 as illustrated in FIGS. 1 and 4, and in solid line in FIG. 2. The retractor 14 may then be rotated relative to the ring holder 12 about the axle 15. The operator may then move the washers 16,18 into contact with another to allow the serrations 20, 22 to cooperate as illustrated to the second configuration by rotating the cam actuator 17 about clamping pivot 19 as shown in phantom in FIG. 2.

If the spring biases the washers 16,18 into the second position in other embodiments, it may be desirable to allow for the radial alignment of the retractor holder 14 relative to the ring holder 12 to be selected in another manner. Specifically, the operator may pull the washers 16,18 apart, and rotate to the desired position, and then allow the spring to pull the washers 16,18 back together.

The mechanics of the rotation and locking about the axle 15 may best be understood by referring to FIG. 3. The clamping pivot 19 is illustrated as parallel to the axle 15. The axle 15 contains groove 21 which preferably has a groove surface 23 parallel to groove surface 25. The groove surfaces 23,25 are in planes, perpendicular to the axis of the axle 15. The axis of the axle 15 may also be referred to as a rotation axis. The axle 15 is also connected to or comprised of spring member 24. The base 26 is placed over the axle 15 with groove 21 accessible through slot 27. The cam actuator 17 is then placed so that cam surface 29 and clamping pivot 19 extend into the slot where the cam surface 29 is operable with the groove 21. The clamping pivot 19 is then secured with a retaining member such as Add a pin 11 shown in FIG. 2. As the cam actuator 17 is moved as shown in FIG. 2 (in phantom), the cam surface 29 acts against the groove surface 25 causing the bottom surface 31 to exert a downward force against the slot bottom 33 and to force the washers 16,18 together in the second, or locked, configuration. Movement of the cam actuator 17 in the opposite direction releases the force. A spring member 24 may assist in separating the washers 16,18. Accordingly, the spring member 24 biases the rotational element in the first configuration.

In other embodiments, the rotational element may not be biased in either of the first or second configurations, or the rotational element maybe biased in the second configuration. Furthermore, in other embodiments, the rotational element may not have a second configuration, and remain in the first configuration allowing the retractor holder 14 to instantly rotate relative to the ring holder 12 without releasing a locking mechanism.

In the preferred embodiment, one of the opposing washers 16 is connected to the ring holder 12 at a top surface of the ring holder 12 and the other washer 18 is connected to a base 26. The base 26 also preferably includes a toothed hub 28 which assists the retractor holder 14 in being pivotally positioned relative to the ring holder 12. The toothed hub 28 is press fit into the base 26. The base 26 has a base pivot 30 which connects the retractor holder 14 to the base 26 while providing a pivot point for directing the blade of a retractor (not shown) to a specific depth in an opening. The toothed hub 28 fits within passage 37 in the retractor holder 14 and assists in selecting a pivot angle of the retractor holder 14 relative to the base 26.

The retractor holder 14 preferably includes a lock mechanism 32 which is moveable between a locking position and an unlocked position. In the locking position at least one grip 34 engages the toothed hub 28 to provide a desired angular position of pivot of the retractor holder 14 relative to the ring holder 12. An actuation lever 76 may be utilized to pivot the grip 34 in and out of engagement with a portion of the toothed hub 28 about pivot 78. A spring is preferably utilized to bias the locking mechanism 32 in locking engagement with the toothed hub 28 as shown in FIG. 4. The retractor holder 14 also preferably contains a rectangular bore 36 for receiving the stem 38 of a retractor blade as shown in FIGS. 2 and 4. The retractor stem 38 may be held in fixed relation to the retractor holder 14 by the pawl blade 40 of the pawl 42. The pawl 42 is preferably spring biased to engage the retractor stem 38 by a spring. The pawl 42 has an actuation lever 80 which pivots about pivot 82 to engage and disengage the pawl blade 40.

In addition for allowing for rotation of the retractor holder 14 relative to the ring holder 12, the preferred embodiment also employs a ring holder 12 which secures the mechanism 10 to the ring 46 with a retention mechanism 48 as shown in FIGS. 1–3. The retention mechanism 48 is preferably actuated by a lever 50 which is spring biased to retain the ring 46 within a transverse slot 54. Although the preferred embodiment has a retention mechanism 48 attached to a lever 50 for retaining an end 56 of the width of the ring 46 within the transverse slot 54, other locations along the width of the ring 46 could also be retained by a retention mechanism 48. Furthermore, the retention mechanism 48 need not necessarily be equipped with a release lever 50 in all embodiments. The retention mechanism 48 may also include one or more surfaces in the transverse slot 54, such as opposing slot surfaces, which move to secure the ring 46 in the slot 54.

The retention mechanism 48 illustrated rotates about retention pivot 60 and is preferably spring biased in the retaining position shown in FIGS. 1 and 2. Depression of the lever 50 moves the retention mechanism 48 about the retention pivot 60 to allow the ring 46 to be inserted into the transverse slot 54. An arm 62 extending between the retention mechanism 48 and the retention pivot 60 is at least partly contained housed within notch 64 in the retaining position. The spring 84 may be received within a spring bore 66. An access port 68 allows access within the ring holder 12 to secure a pin through the retention pivot 60. Springs for the locking mechanism 32 and pawl mechanism 42 may be similarly located on those structures.

The locking mechanism 32 and the pawl 42 operate in a similar manner as the retention mechanism, however in alternative embodiments, different designs may provide for different operation of these members.

In order to ensure a snug fit for the ring 46 in the transverse slot 54, a spring member 70 is placed at least partially through a bore (obscured from view) in the ring holder 12. A retaining plate 72 keeps the spring member 70 in position so that plunger 74 contacts the inserted ring member 46 and exerts a force so that the ring member 46 is contacted by the plunger 74 and the retention mechanism 48. The spring member 70 is preferably under compression when the ring member 46 is installed to positively retain ring against retention mechanism 48 having lip 86.

Figure 5:
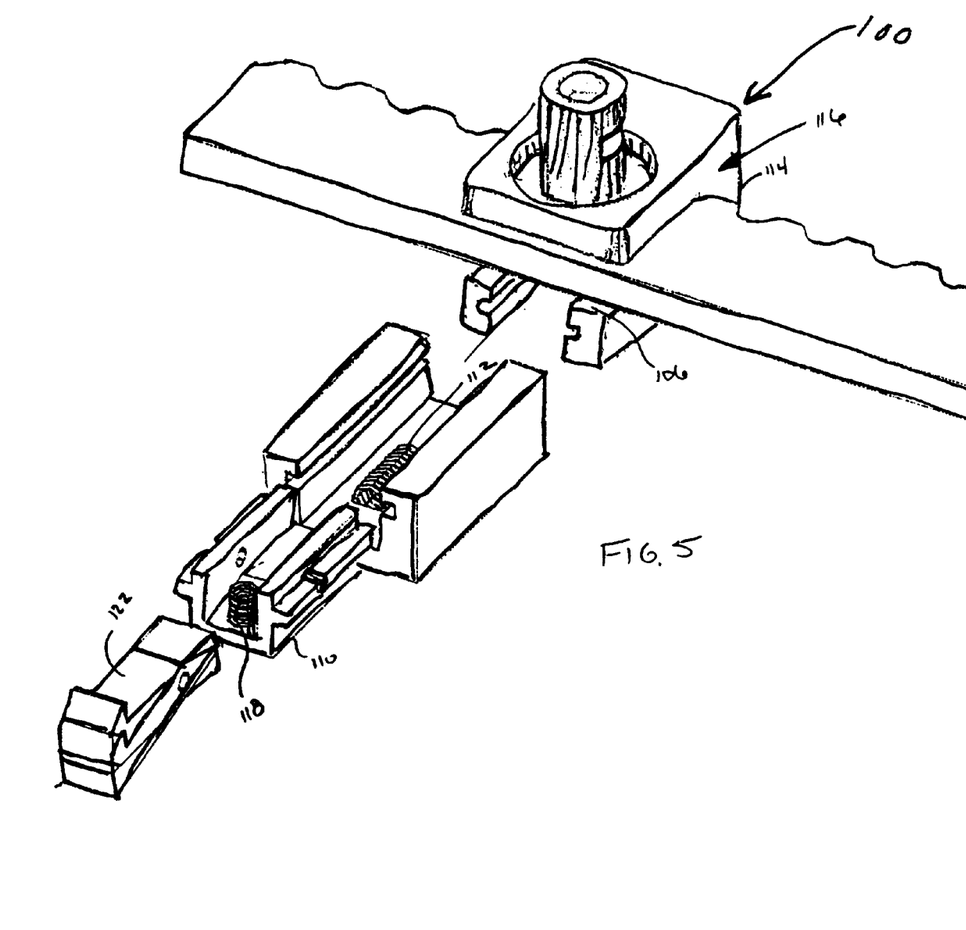
FIG. 5 shows an exploded cutaway top elevational view of an alternative embodiment of a portion of a locking mechanism utilized in a ring holder.
Figure 6:
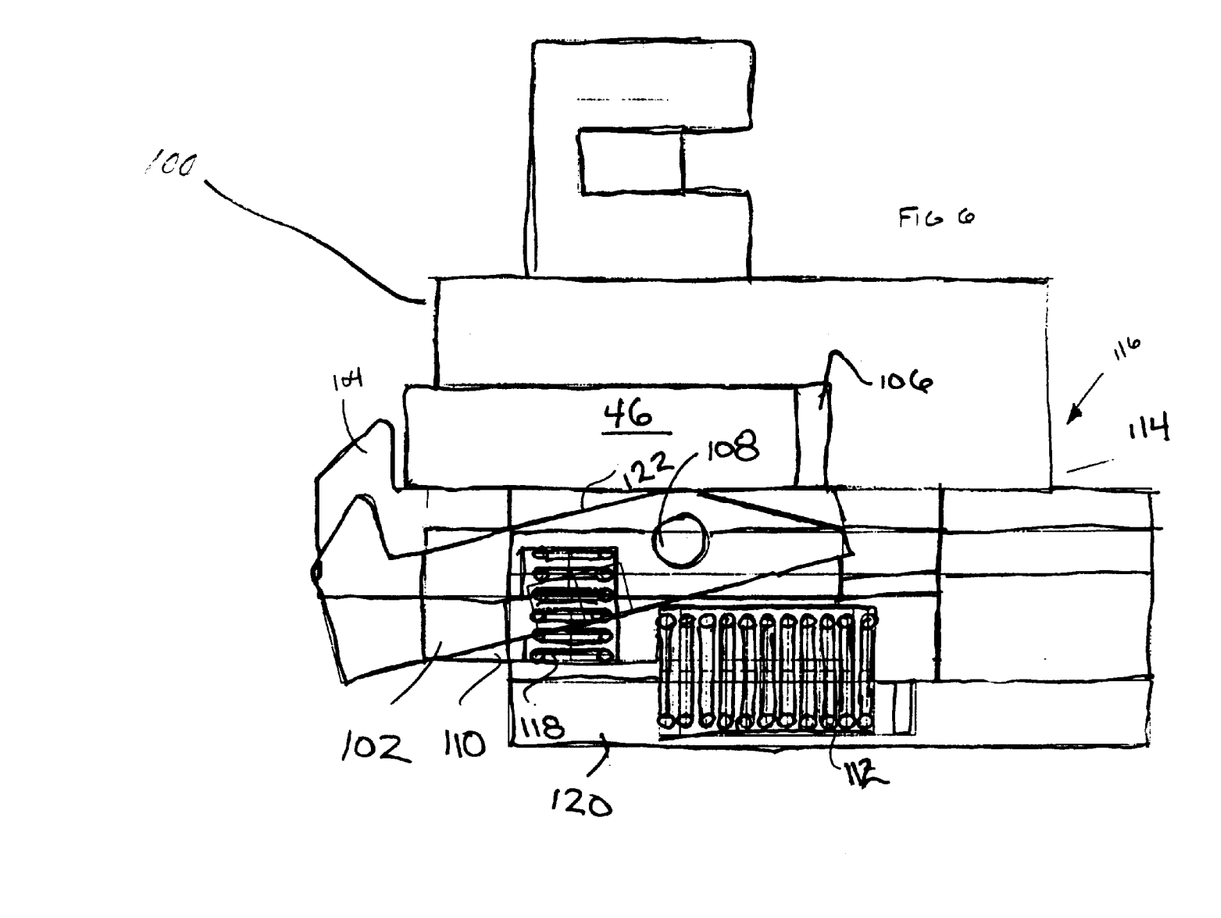
FIG. 6 shows a side cross sectional view of the alternative embodiment of FIG. 5 in use.

FIGS. 5 and 6 show an alternatively preferred retention mechanism 100. In this embodiment, a pivoting arm 102 with a stop 104 retains ring 46 in a transverse slot 106 which is similar to the transverse slot 54 of the preferred embodiment. The arm 102 is moveable about pivot 108 to allow a ring 46 to be inserted into the slot. The pivot 108 is preferably connected to slide 110 which is spring biased by spring 112 to a first end 114 of the ring holder 116. The arm 102 illustrated is biased into a locking position by spring 118. The slide 110 is moveable within housing 120 which is connected, and preferably an integral portion of the ring holder 116.

The slide 110 allows the retention mechanism 100 to accommodate a plurality of ring widths. FIG. 6 shows the operation of the arm 102 in a downward direction to release the ring 46 from the slot 106. A top surface 122 of the arm 102 contacts the ring 46 in compression to retain the ring 46 in the slot 106. Furthermore, the stop 104 retains the ring 46 from sliding out of the slot 106.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

What is claimed is:

1. A multi-position ratchet mechanism comprising:
   a ratchet holder having a passage within the ratchet holder and a retractor slot extending through the retractor holder;
   a locking mechanism connected to said ratchet holder and having a grip actuation lever extending outside of said passage for ready actuation by a user, said locking mechanism having a grip normally biased into said passage, and operation of the grip actuation lever moving the grip out of the passage;
   a base pivotably connected at a base pivot to the ratchet holder about a pivot axis;
   a ratchet extending from said base into said passage of said ratchet holder and operatively engaging said grip whereby a pivot angle of the ratchet holder with respect to said base may be selectively varied;
   a pawl connected to said ratchet holder and having a pawl actuation lever extending outside of said retractor slot for ready actuation by a user, said locking mechanism having a pawl blade normally biased into said retractor slot, and operation of the pawl actuation lever moving the pawl blade out of the retractor slot; and
   a ring holder having a ring slot, said ring holder rotatable relative to the base about a rotation axis in a first configuration; said rotation axis non-colinear with said pivot axis.

2. The multi-position ratchet mechanism of claim 1 wherein the ring holder further comprises a retaining mechanism configured to selectively positively retain a ring within the slot.

3. The multi-position ratchet mechanism of claim 2 wherein the retaining mechanism is connected to an arm and a lever, whereby actuation of the retaining mechanism moves the retaining mechanism into and out of a holding position.

4. The multi-position ratchet mechanism of claim 1 wherein the ring holder has a top surface and the base has a bottom surface, the top surface of the ring holder rotating parallel to the bottom surface of the base in the first configuration, and the ratchet holder pivots about the pivot axis orthoganally to the rotation axis.

5. The multi-position ratchet mechanism of claim 1 further comprising a locking actuator, said locking actuator having a locking position wherein said base and said ring holder are selectively locked at a rotation angle relative to one another in a second configuration.

6. A multi-position ratchet mechanism comprising:
   a ratchet holder having a passage within the ratchet holder and a retractor slot extending through the retractor holder;
   a locking mechanism connected to said ratchet holder and having a grip actuation lever extending outside of said passage for ready actuation by a user, said locking mechanism having a grip normally biased into said passage, and operation of the grip actuation lever moving the grip out of the passage;
   a base pivotably connected at a base pivot to the ratchet holder;
   a ratchet extending from said base into said passage of said ratchet holder and operatively engaging said grip whereby a pivot angle of the ratchet holder with respect to said base may be selectively varied;
   a pawl connected to said ratchet holder and having a pawl actuation lever extending outside of said retractor slot for ready actuation by a user, said locking mechanism having a pawl blade normally biased into said retractor slot, and operation of the pawl actuation lever moving the pawl blade out of the retractor slot;
   a ring holder having a ring slot, said ring holder rotatable relative to the base in a first configuration; and
   a plunger spring biased into the ring slot.

7. The multi-position ratchet mechanism of claim 6 further comprising a retention mechanism located at least partially external to the ring slot, said retention mechanism selectively operable between a lock and unlock position, where when in said lock position, an inserted ring contacts the plunger and the retention member.

8. A multi-position ratchet mechanism comprising:
   a retractor holder having a retractor slot extending through a portion of the retractor holder;
   a pawl operably coupled to the retractor holder having a retaining and a release position, wherein when said pawl is placed in said retaining position, said pawl retains an inserted retractor stem relative to the retractor holder;
   a base pivotably connected to the retractor holder at a base pivot; and
   a ring holder having a top surface portion and a slot configured to receive a ring member, said ring holder operably coupled to the base, said base rotatable about a rotation axis relative to the ring holder in a first configuration along the top surface portion of the ring holder, said base fixed at an angular position relative to the ring holder in a second configuration; said retractor holder pivots through an arc in a pivot plane perpendicular to the base pivot, the base rotates through a plane of rotation perpendicular to the rotation axis, and said pivot plane is substantially orthogonal to said plane of rotation in the first configuration.

9. The multi-position ratchet mechanism of claim 8 further comprising a locking mechanism configured to selectively set a pivot angle of the ratchet holder relative to the base.

10. The multi-position ratchet mechanism of claim 8 wherein the base has a planar bottom surface portion and the ring holder has a planar top surface portion, and said planar bottom surface portion of said base rotates parallel to the planar top surface portion of the ring holder in the first configuration.

11. The multi-position ratchet mechanism of claim 8 further comprising a locking actuator, said locking actuator having a locking position wherein said base and said ring holder are selectively locked at a rotation angle relative to one another in a second configuration.

12. A multi-position ratchet mechanism comprising:
   a retractor holder having a retractor slot extending through a portion of the retractor holder;
   a pawl operably coupled to the retractor holder having a retaining and a release position, wherein when said pawl is placed in said retaining position, said pawl retains an inserted retractor stem relative to the retractor holder;
   a base connected to the retractor holder; and
   a ring holder having a top surface portion and a slot configured to receive a ring member, said ring holder operably coupled to the base, said base rotatable about a rotation axis relative to the ring holder in a first configuration along the top surface portion of the ring holder, said base fixed at an angular position relative to the ring holder in a second configuration;
   a locking actuator having a locking position wherein said base and said ring holder are selectively locked at a rotation angle relative to one another in a second configuration, said locking actuator further comprising a cam surface rotatable about a locking pivot, and rotation of the cam surface in a direction of rotation about the locking pivot locks the base relative to the ring holder at the rotation angle.

13. A multi-position ratchet mechanism comprising:
   a retractor holder having a retractor slot extending through the retractor holder;
   a pawl operably coupled to the retractor holder having a retaining and a release position, wherein when said pawl is placed in said retaining position, said pawl retains an inserted retractor stem in a fixed position relative to the retractor holder;
   a base pivotably connected to the retractor holder at a base pivot about a pivot axis;
   a ring holder having a ring slot configured to receive a ring member, said ring holder connected to the base, said pivot axis parallel to the ring slot; and
   a retention mechanism connected to the ring holder and selectively operable to retain and release an inserted ring relative to the ring slot.

14. The multi-position ratchet of claim 13 wherein the ring holder is operably coupled to the base, wherein the base is rotatable relative to the ring holder in a first configuration and held at a fixed rotation angle relative to the ring holder in a second configuration.

15. The multi-position ratchet of claim 13 further comprising a spring member operably coupled to the ring holder having a plunger at least partially located within the ring slot, said plunger and said retainer mechanism cooperating to retain an inserted ring in the ring slot.

16. A multi-position ratchet mechanism comprising:
   a retractor holder having a retractor slot extending through the retractor holder;
   a pawl operably coupled to the retractor holder having a retaining and a release position, wherein when said pawl is placed in said retaining position, said pawl retains an inserted retractor stem in a fixed position relative to the retractor holder;
   a base pivotably connected to the retractor holder at a base pivot about a pivot axis;
   a ring holder having a ring slot configured to receive a ring member, said ring holder operably coupled to the base, wherein the base is rotatable relative to the ring holder in a first configuration and held at a fixed rotation angle relative to the ring holder in a second configuration; and
   a retention mechanism connected to the ring holder and selectively operable to retain and release an inserted ring relative to the ring slot; and
   a locking mechanism selectively operable to select the fixed rotation angle through a range of at least ninety degrees.

17. The multi-position ratchet of claim 16 further comprising an axle coupling the base to the ring holder, said axle extending along a rotation axis with the base rotatable about the rotation axis.

18. The multi-position ratchet of claim 17 further comprising contact surfaces located between the base and the ring holder said contact surfaces separated in a first configuration allowing rotation of the ring holder relative to the base about the axle.

19. The multi-position ratchet of claim 18 wherein the contact surfaces contact one another in a second configuration to prevent rotation of the ring holder relative to the base.

20. The multi-position ratchet of claim 19 further comprising a cam actuator operably coupled to one of the base and ring holder, said cam actuator movable between a locked and an unlocked position wherein when in said locked position, said contact surfaces are moved in contact with one another.

21. The multi-position ratchet of claim 20 further comprising a slot in the base having a slot bottom, and said cam actuator having a cam surface and a bottom surface pivotable about a locking pivot, said slot receiving the cam surface and bottom surface, and said axle further comprising a groove, said groove receiving said cam surface wherein when said cam actuator moves from the first position to the second position, the bottom surface of the cam actuator applies a force against the slot bottom thereby forcing the contact surfaces in contact with one another.

22. The multi-position ratchet of claim 21 wherein said contact surfaces are biased in one of the first and second configurations.

23. A multi-position ratchet mechanism comprising:
   a retractor holder having a retractor slot extending through the retractor holder;
   a pawl operably coupled to the retractor holder having a retaining and a release position, wherein when said pawl is placed in said retaining position, said pawl retains an inserted retractor stem in a fixed position relative to the retractor holder;
   a base pivotably connected to the retractor holder at a base pivot;
   a ring holder having a ring slot configured to receive a ring member, said ring holder connected to the base; and
   a retention mechanism connected to the ring holder and selectively operable to retain and release an inserted ring relative to the ring slot; and
   a toothed hub connected to one of the base and retractor holder, said toothed hub cooperating with a locking mechanism having a grip, said grip operatively engaging the toothed hub whereby a pivot angle of the ratchet holder with respect to said base may be selectively varied.

\* \* \* \* \*